United States Patent
Underhill et al.

(10) Patent No.: US 6,911,228 B2
(45) Date of Patent: Jun. 28, 2005

(54) PROCESS FOR MANUFACTURING A TOILET TRAINING ARTICLE

(75) Inventors: Richard L. Underhill, Neenah, WI (US); Marsha M. Malone, Appleton, WI (US); Bernard J. Minerath, III, Oshkosh, WI (US); Beth A. Lange, Germantown, TN (US); Duane G. Krzysik, Appleton, WI (US); David W. Koenig, Menasha, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 28 days.

(21) Appl. No.: 10/456,330

(22) Filed: Jun. 6, 2003

(65) Prior Publication Data

US 2004/0015143 A1 Jan. 22, 2004

Related U.S. Application Data

(62) Division of application No. 09/696,737, filed on Oct. 25, 2000, now Pat. No. 6,657,100.

(51) Int. Cl.⁷ .............................. A61L 24/00; B05D 3/00
(52) U.S. Cl. ...................... 427/2.31; 427/2.1; 427/2.3; 427/355; 427/356; 427/357; 427/421
(58) Field of Search .................. 427/2.1, 2.3, 2.31, 427/355–357, 421

(56) References Cited

U.S. PATENT DOCUMENTS

| | | |
|---|---|---|
| 479,836 A | 8/1892 | Parks |
| 3,338,992 A | 8/1967 | Kinney |
| 3,341,394 A | 9/1967 | Kinney |
| 3,490,454 A | 1/1970 | Goldfarb et al. |
| 3,502,538 A | 3/1970 | Petersen |
| 3,502,763 A | 3/1970 | Hartmann |
| 3,542,615 A | 11/1970 | Dobo et al. |
| 3,585,998 A | 6/1971 | Hayford et al. |
| 3,691,271 A | 9/1972 | Charle et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,597,960 A | 7/1986 | Cohen |
| 4,750,482 A * | 6/1988 | Sieverding .................. 604/317 |
| 4,790,836 A | 12/1988 | Brecher |
| 4,842,593 A | 6/1989 | Jordan et al. |

(Continued)

FOREIGN PATENT DOCUMENTS

| | | |
|---|---|---|
| FR | 2786396 A1 | 6/2000 |
| JP | 59-106501 | 6/1984 |
| JP | 11-178854 | 7/1999 |
| WO | WO 00/37009 | 6/2000 |
| WO | WO 00/64500 | 11/2000 |
| WO | WO 02/34176 A2 | 5/2002 |
| WO | WO 02/34189 A2 | 5/2002 |

OTHER PUBLICATIONS

PCT/US01/29222 PCT International Search Report Completed Apr. 17, 2002.

*Primary Examiner*—Jennifer Michener
(74) *Attorney, Agent, or Firm*—Senniger Powers

(57) ABSTRACT

A process for manufacturing a toilet training article in the form of a toilet training pad containing an astringent agent or source thereof is disclosed. The toilet training pad, which may be an insertable pad or integrated directly into an undergarment, contains an astringent agent or source thereof which does not contact the wearer's skin until urination occurs at which time a tingling or other sensation is felt on the skin. To prevent contact of the astringent agent with the wearer's skin until urination, the astringent agent may be microencapsulated into a dissolvable shell or may be inserted into a microsponge.

18 Claims, 4 Drawing Sheets

U.S. PATENT DOCUMENTS

| | | |
|---|---|---|
| 4,940,464 A | 7/1990 | Van Gompel et al. |
| 5,073,365 A | 12/1991 | Katz et al. |
| 5,558,874 A | 9/1996 | Haber et al. |
| 5,649,914 A | 7/1997 | Glaug et al. |
| 5,658,268 A | 8/1997 | Johns et al. |
| 5,681,298 A | 10/1997 | Brunner et al. |
| 5,681,574 A | 10/1997 | Haber et al. |
| 5,702,376 A | 12/1997 | Glaug et al. |
| 5,702,377 A | 12/1997 | Collier, IV et al. |
| 5,766,389 A | 6/1998 | Brandon et al. |
| 5,797,892 A | 8/1998 | Glaug et al. |
| 5,869,075 A | 2/1999 | Krzysik |
| 5,885,264 A | 3/1999 | Matsushita |
| 5,891,124 A | 4/1999 | Nomura et al. |
| 6,200,374 B1 * | 3/2001 | Stevens .................. 106/217.7 |
| 6,369,290 B1 * | 4/2002 | Glaug et al. ................ 604/359 |
| 6,410,821 B1 | 6/2002 | Roe |
| 6,433,244 B1 | 8/2002 | Roe et al. |
| 2002/0087129 A1 | 7/2002 | Di Lucio et al. |

\* cited by examiner

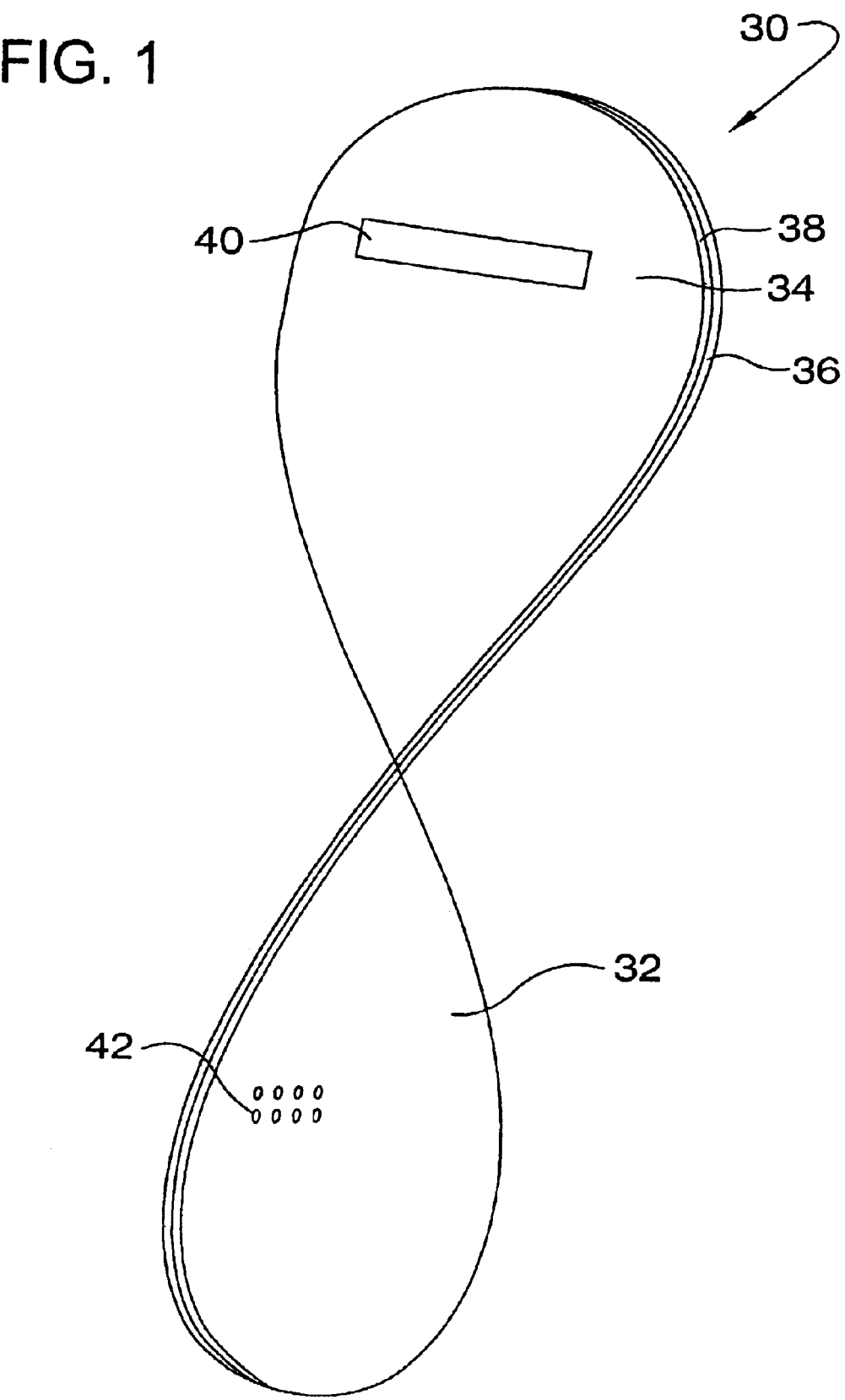

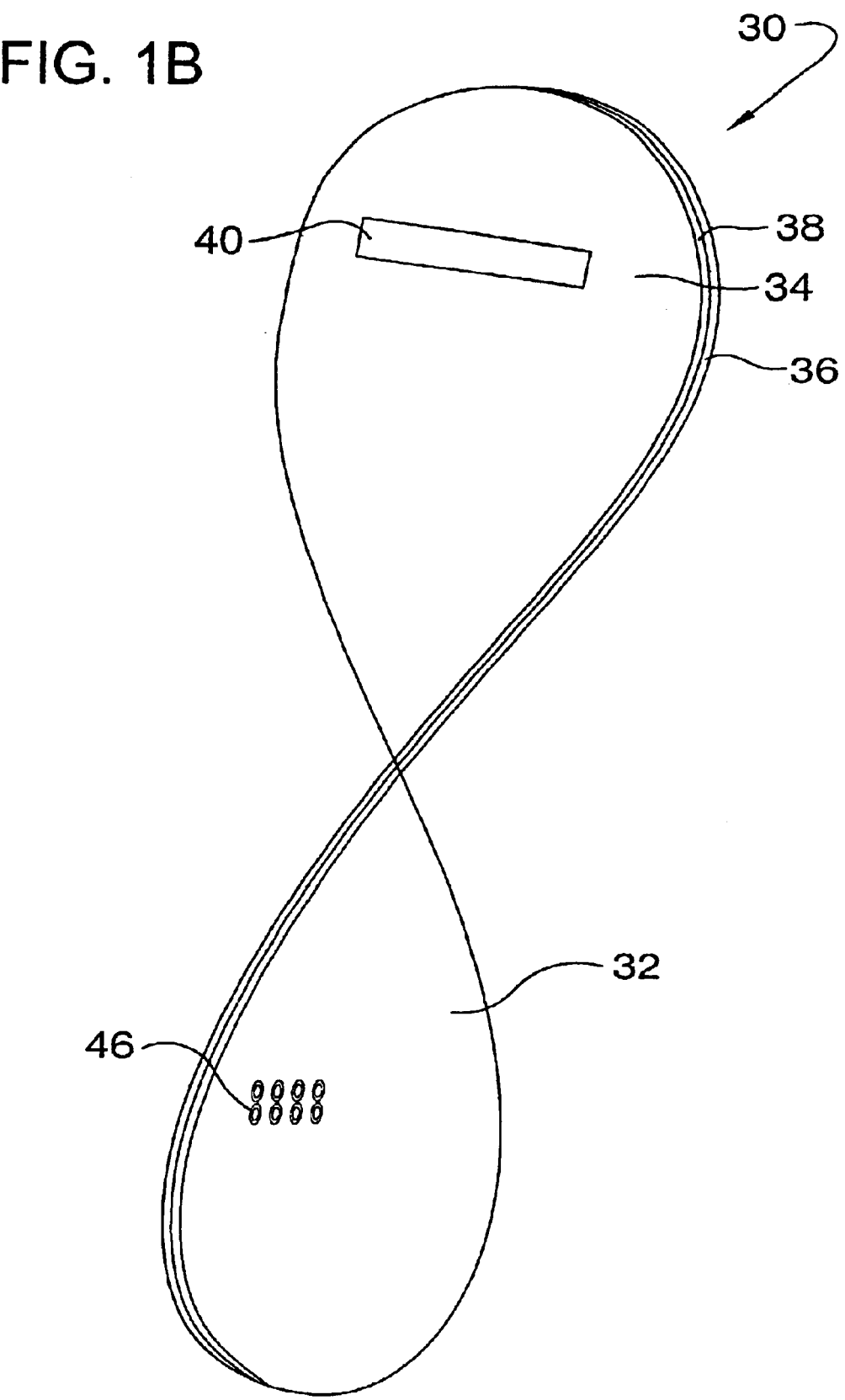

PROCESS FOR MANUFACTURING A TOILET TRAINING ARTICLE

CROSS REFERENCE TO RELATED APPLICATION

This patent application is a divisional patent application of U.S. patent application Ser. No. 09/696,737 filed on Oct. 25, 2000, and allowed on May 2, 2003, now U.S. Pat. No. 6,657,100, which is incorporated in its entirety.

BACKGROUND OF THE INVENTION

The present invention relates to an article for assisting humans, particularly children, in toilet training. More specifically, the present invention relates to an article in the form of a pad containing an astringent agent or a source thereof which when worn facilitates the toilet training process by providing a tingling or other sensation to the skin of the wearer after urination occurs.

Disposable absorbent training pants are useful in toilet training children. Typically, these undergarments are similar to washable, cloth underwear in how they are put on and worn, yet also provide an absorbent function like diapers to draw and retain urine away from the skin of the wearer. Training pants provide a child undergoing toilet training with an undergarment which eases the transition from diapers to washable, cloth underwear as they become more confident in their ability to use the toilet independently.

In order to learn to use the toilet independently, a child must first recognize when urination has occurred so that this bodily function may be controlled. This recognition can represent a substantial hurdle in the training process as urination may often occur during an activity that distracts the child sufficiently so that the child does not notice urination. Also, a child's ability to recognize when urination occurs may be hampered by the improved performance of disposable absorbent undergarments which quickly draw and retain urine away from the wearer's skin after an insult occurs.

Many believe that a child must feel the sensation of wetness on the skin after urination in order to facilitate awareness of this bodily function and promote timely use of the toilet so as to avoid the uncomfortable feeling which otherwise follows. Although this belief is embraced by many, such practice may expose a child to increased risk of skin irritations and rashes caused by prolonged and repeated contact with urine.

Several attempts have been made at providing toilet training aids which alert a child that urination has occurred. For example, pads adapted for releasable attachment to a disposable toilet training pant, diaper or other undergarment and including a temperature change member and/or a dimensional change member which provide a temperature change or dimensional change sensation when contacted with urine to alert the child wearing the undergarment that urination has occurred have been fabricated. Also, absorbent articles are disclosed that when first insulted, have a high initial surface moisture value or wet feel to alert the child that urination has occurred. This initial wetness lasts only a short time after which the surface moisture value drops to a lower level resulting in a drier feeling to the child and increased comfort.

Although there has been substantial progress in toilet training aids, there continues to be a need for simple, effective articles that alert children that urination has occurred.

SUMMARY OF THE INVENTION

The present invention concerns a process for manufacturing a toilet training pad which alerts the wearer that urination has occurred. The toilet training pad may be an integral part of an undergarment, or may be a pad that can be releasably attached to an undergarment by a purchaser. The pad contains an astringent agent or a source thereof that alerts the wearer that urination has occurred by causing a tingling, tightening, or other sensation on the skin upon urination. This may be accomplished, if desired, without trapping moisture against the skin of the wearer. The present invention can be used in a variety of absorbent undergarments.

Briefly, therefore, the present invention is further directed to a process for manufacturing an article in the form of a pad comprising a pliable substrate and an astringent agent or source thereof. The process comprises first mixing the astringent agent or source thereof with an adhesive and then applying the mixture onto the substrate and allowing the mixture to dry.

Other embodiments and features of this invention will be in part apparent and in part pointed out hereinafter.

BRIEF DESCRIPTION OF THE DRAWINGS

FIG. 1 is a perspective view of a pliable toilet training pad in accordance with the present invention.

FIG. 1B is a perspective view of a pliable toilet training pad in accordance with one embodiment of the present invention.

Corresponding reference characters indicate corresponding parts throughout the drawings.

DEFINITIONS

Figure 1A:
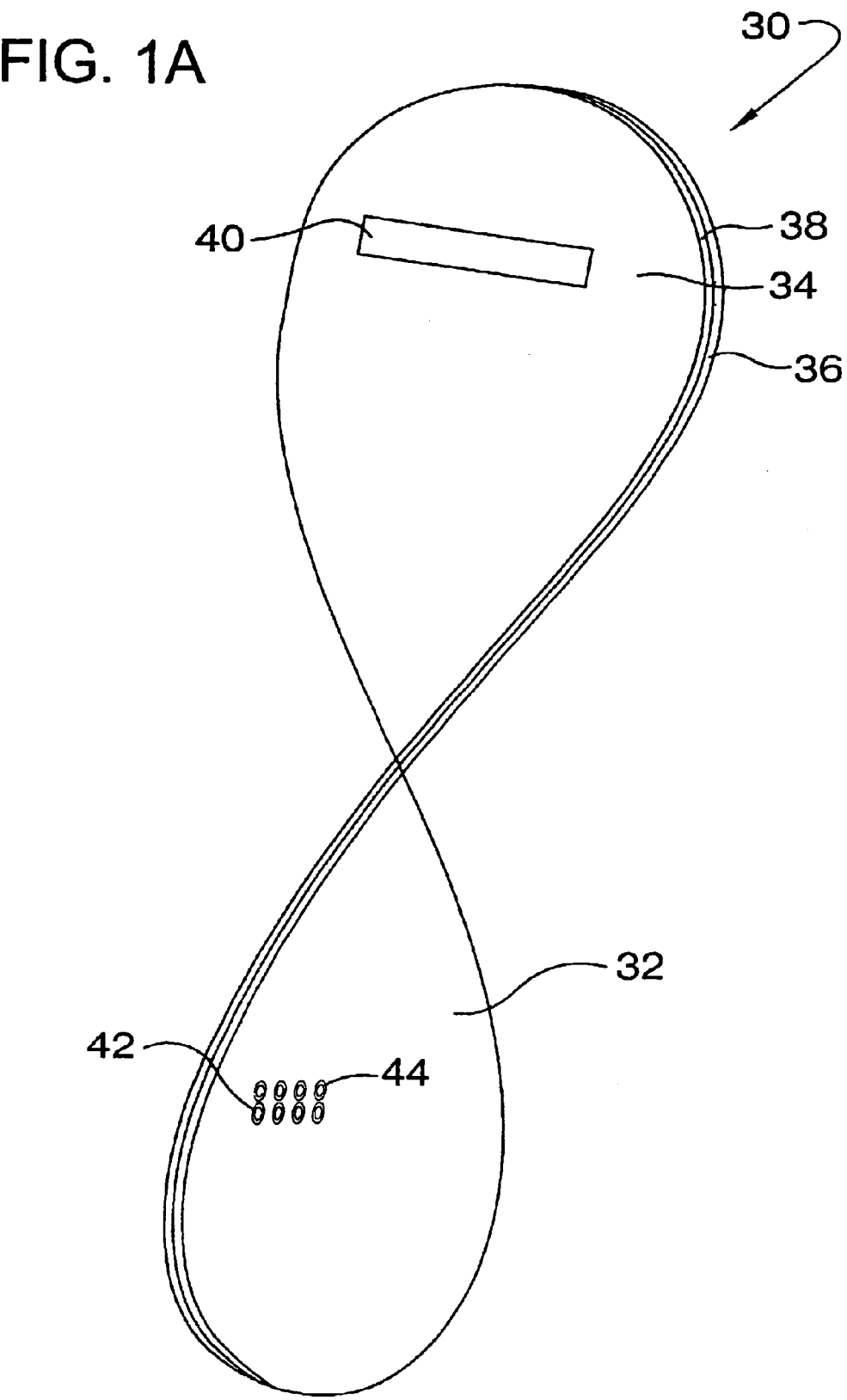
FIG. 1A is a perspective view of a pliable toilet training pad in accordance with one embodiment of the present invention.

Within the context of this specification, each term or phrase below will include the following meaning or meanings:

(a) "Bonded" refers to the joining, adhering, connecting, attaching, or the like, of two elements. Two elements will be considered to be bonded together when they are bonded directly to one another or indirectly to one another, such as when each is directly bonded to intermediate elements.

(b) "Disposable" refers to articles which are designed to be discarded after a limited use rather than being laundered or otherwise restored for reuse.

(c) "Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

(d) "Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "non-wettable" or hydrophobic.

(e) "Integrated" is used to refer to various portions of a single unitary element rather than separate structures bonded to or placed with or placed near one another.

(f) "Layer" when used in the singular can have the dual meaning of a single element or a plurality of elements.

(g) "Liquid impermeable," when used in describing a layer or multi-layer laminate means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

(h) "Liquid permeable" refers to a material present in one or more layers, such as a film, nonwoven fabric, or open-celled foam, which is porous, and which is water permeable due to the flow of water and other aqueous liquids, such as urine, through the pores. The pores in the film or foam, or spaces between fibers or filaments in a nonwoven web, are large enough and frequent enough to permit leakage and flow of liquid water through the material.

(i) "Meltblown" refers to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

(j) "Nonwoven" and "nonwoven web" refer to materials and webs of material which are formed without the aid of a textile weaving or knitting process.

(k) "Pliable" refers to materials which are compliant and which will readily conform to the general shape and contours of the wearer's body.

(l) "Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and atactic symmetries.

(m) "Spunbond" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, more particularly, between about 0.6 and about 10.

(n) "Superabsorbent" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

(o) "Surface" includes any layer, film, woven, nonwoven, laminate, composite, or the like, whether pervious or impervious to air, gas, and/or liquids.

(p) "Surge Layer" refers to a layer typically comprised of nonwoven materials that can absorb a large stream or gush of liquid and release it slowly into another layer or layers.

(q) "Thermoplastic" describes a material that softens when exposed to heat and which substantially returns to a nonsoftened condition when cooled to room temperature.

(r) "Three dimensional" refers to a garment similar to underwear, shorts or pants in that it has continuous leg and waist openings that are bounded by material of which the garment is made. The garment may or may not have manually tearable seams.

DETAILED DESCRIPTION OF THE PREFERRED EMBODIMENTS

In accordance with the present invention, it has been discovered that an astringent agent or a source thereof can be strategically positioned in a child's toilet training pant or other undergarment such that upon urination the astringent agent contacts the skin and induces a tingling or other sensation on the skin of the wearer to alert the wearer that urination has occurred. The toilet training article in accordance with the present invention can be used in conjunction with an absorbent undergarment to alert the wearer that urination has occurred while reducing potential adverse effects of prolonged contact between the skin and voided urine. Although discussed primarily in the context of toilet training of children, it should be understood that the present invention and its function are also applicable as an adult personal care product such as in absorbent incontinence undergarments and the like.

Referring to FIG. 1, there is shown a pliable toilet training pad 30 in accordance with the present invention. The toilet training pad comprises a pliable substrate having a body side 32 and an outer side 34. The body side faces the skin of the wearer during wear, generally in the crotch and/or buttocks region, while the outer side faces away from the skin of the wearer. As illustrated in FIG. 1, the toilet training pad is of layered construction and comprises a liner layer 36 and an absorbent core layer 38. Although illustrated in FIG. 1 with layered construction having two distinct, separate layers, and discussed herein primarily as having a liner and an absorbent core layer, it should be recognized that the toilet training pad of the present invention could be comprised of a single layer substrate comprised of, for example, a liner, or may be comprised of numerous different layers which may vary in absorbent capacity, thickness, material of construction, intended purpose, etc. Again referring to FIG.

1, outer side 34 may optionally contain attachment means 40 for releasably attaching the toilet training pad to an undergarment, such as a disposable undergarment. A source of an astringent agent 42 is typically supported on a substrate comprising at least a part of the body face 32 of the toilet training pad such that upon urination, the astringent agent may contact the skin of the wearer and induce a tingling, tightening, or other sensation. It should be recognized, however, that the astringent agent or a source thereof may be located on or within the outer layer, or any other layer or layers comprising the toilet training pad.

Referring now to FIG. 1A, there is shown a pliable toilet training pad 10 similar to that illustrated in FIG. 1 with the exception that the astringent agent or source thereof 42 is shown encapsulated within encapsulation material 44 which may be, for example, a carbohydrate-based material as discussed further below.

The substrate component of the astringent or astringent source containing toilet training pad of the present invention may be a single layer or may be of layered construction and may be comprised of a plurality of fibers which may be woven, nonwoven, or a combination thereof. The fibers may be bi-component, hollow, natural or synthetic, or a combination thereof, and may be hydrophilic or hydrophobic in nature, and may be, for example, a short staple fiber or a longer more continuous fiber generally found in meltblown and spunbond webs. Other suitable webs include bonded carded webs, air laid webs, wet laid webs, solution spun webs, porous films, and generally any porous webs which have sufficient strength to be used as a liner for personal care absorbent products. Polyolefins, polyesters, cellulosics, polyacetates, and polyacrylate thermoplastics are some examples of polymers from which the fibers can be formed. One or more layers of the toilet training pad substrate may be liquid permeable and comprised of, for example, a liquid permeable film, tissue, fabric, or the like. One or more layers may also be liquid impermeable and comprised of, for example, a web or sheet of plastic film such as polyethylene, polypropylene, polyvinyl chloride, or similar material, or a nonwoven, fibrous web which has been suitably constructed and arranged to be substantially liquid impermeable. The toilet training pad of the present invention may also contain one or more superabsorbent and/or surge layers which may be used alone or in combination with one or more layers described above.

As used herein, an astringent agent means a substance that produces a tingling or other sensation and/or tightening of the skin when it contacts human skin. Astringent agents useful in the present invention may be either in liquid or solid form, or a combination of a liquid and a solid. Astringent properties which make a substance useful in the present invention include the ability to tighten the skin and cause a tingling or other sensation upon skin contact. Generally, the more potent the astringent agent, the faster and more acute the tingling or tightening of the skin. Typically, from about 0.01 grams to about 15 grams, preferably from about 0.1 grams to about 10 grams of astringent agent are incorporated into the toilet training pad of the present invention to alert the wearer that urination has occurred. It will be recognized by one skilled in the art that the amount of astringent agent utilized may vary depending upon the location of the astringent agent in the garment in which it is utilized. Suitable astringent agents for use with the toilet training pad of the present invention include, for example, *acacia concinna* extract, *acacia farnesiana* extract, *acacua decyrrens* extract, *alchemilla vulgaris* extract, aluminum acetate, aluminum chloride, aluminum chlorohydrate, aluminum chlorohydrex, aluminum citrate, aluminum diacetate, aluminum dichlorohydra, aluminum glycinate, aluminum lactate, aluminum sesquichlorohydrate, aluminum sulfate, aluminum zirconium octachlorohydrate, aluminum zirconium pentachlorohydrate, aluminum zirconium tetrachlorohydrate, aluminum zirconium trichlorohydrate, apple (*pyrus malus*) extract, *astragalus sinicus* extract, *astrocaryum murumuru* extract, *astrocaryum tucuma* extract, *azadirachta indica* extract, azelamide MEA, bearberry (*arctostaphylos uva-ursi*) extract, birch (*betula alba*) leaf extract, *catalpa kaempfera* extract, *celastrus paniculata* extract, chinese hibiscus (*hibiscus rosa-sinensis*) extract, *coccinea indica* extract, coffee (*coffea arabica*) bean extract, elder (*sambucus nigra*) oil, *euterpe precatoria* extract, evening primrose (*oenothera biennis*) extract, eyebright (*euphrasia officinalis*) extract, gentian (*gentiana lutea*) extract, *geranium maculatum* extract, grape (*vitis vinifera*) leaf extract, henna (*lawsonia inermis*) extract, *hierochloe odorata* extract, honeysuckle (*lonicera caprifolium*) extract, hops (*humulus lupulus*) extract, horsetail (*equisetum arvense*) extract, ivy (*hedera helix*) extract, jujube (*zizyphus jujuba*) extract, *juniperus communis* extract, *kadsura heteliloca* extract, kola (*cola acuminata*) extract, lady's mantle (*alchemilla vulgaris*) extract, lemon bioflavonoids extract, lemon (*citrus medica limonum*) extract, lemon (*citrus medica limonum*) peel extract, *lysimachia foenum-graecum* extract, magnolia spp. extract, *mauritia flexosa* extract, *maximilliana regia* extract, *melaleuca uncinata* extract, *melaleuca wilsonii* extract, *melia australasica* extract, mentha spp, neem (*melia azadirachta*) seed oil, nettle (*urtica dioica*) extract, oak (quercus) bark extract, palmetto extract, passionflower (passiflora) fruit extract, *phyllanthus emblica* extract (or *emblica officinalis*), plantain (*plantago major*) extract, *polygonum multiflorum* extract, *pterocarpus marsupianus* extract, raspberry (rubus) extract, selinum spp. extract, *shorea robusta* extract, sodium alumchlorohydroxy lactate, sodium aluminum lactate, St. John's wort (*hypericum perforatum*) extract, tannic acid, tea (*camellia sinensis*) extract, *vetiveria zizanoides* extract, walnut (*juglans regia*) leaf extract, walnut (*juglans regia*) oil, wheat (*triticum vulgare*) protein, white nettle (*lamium album*) extract, witch hazel (*hamamelis virginiana*) extract, *xanthozylum bungeanum* extract, zinc acetate, zinc chloride, zinc lactate, zinc oxide, zinc sulfate, zirconium chlorohydrate, or a combination of one or more of the above. In particular embodiments, the astringent agents can include calcium chloride, aluminum lactate, ammonium alum, potassium alum, sodium alum, or combinations thereof. It will be recognized by one skilled in the art that other agents that provide neurosensory cues could be added along with the astringent agents disclosed herein and incorporated into a toilet training pad.

Both liquid and solid astringent agents or sources thereof utilized in the present invention may be introduced directly into or onto a face of the toilet training pad or, alternatively, first encapsulated into a shell material which releases the astringent agent or source when wetted with urine. The microencapsulated shell is constructed of a material such that it will release the astringent agent or source upon contact with urine and allow the astringent agent to contact the skin and alert the wearer that urination has occurred through a tingling, tightening, or other sensation. The urine may cause the shell material to solubilize, disperse, swell, disintegrate, or may be urine permeable such that it disintegrates or discharges the astringent agent upon contact with urine. Suitable microencapsulation shell materials include cellulose-based polymeric materials (e.g., ethyl cellulose), carbohydrate-based materials (e.g., starches and sugars) and materials derived therefrom (e.g., dextrins and cyclodextrins) as well as other materials compatible with human tissues. The microencapsulation shell thickness may vary depending upon the astringent agent utilized, and is generally manufactured to allow the encapsulated astringent agent to be covered by a thin layer of encapsulation material, which may be a monolayer or thicker laminate layer, or may be a composite layer. The microencapsulation layer should be thick enough to resist cracking or breaking of the shell during handling or shipping of the product or during wear which would result in breakage of the encapsulation material and a premature release of the astringent agent. The microencapsulation layer should also be constructed such that humidity from atmospheric conditions during storage, shipment, or wear will not cause a breakdown of the microencapsulation layer and result in a release of the astringent agent or source thereof.

Microencapsulated astringent agents, as well as solid astringent agents applied directly to the toilet training aid, should be located or be of a size such that the wearer cannot feel the encapsulated shell or solid against the skin prior to urination. Solid astringent agents utilized neat may be introduced into the fabric of the liner or absorbent core and hence not have direct skin contact prior to urination. For solid astringent agents, average particle sizes of from about 1 micrometer to about 25 micrometers, preferably from about 20 micrometers to about 25 micrometers, are suitable for use in the present invention as these sizes are generally not felt by the wearer should direct contact occur. Although larger particle sizes may be utilized in a microencapsulated shell embodiment, if solid astringent agents are used directly in or on the toilet training pad, sizes less than about 25 micrometers may be desirable as mentioned above to deter any "gritty" or "scratchy" feeling on the skin of the wearer of the pad.

The astringent agents of the present invention, either in neat form, in microencapsulated form or a combination thereof, may be introduced into the liner, the absorbent core, or both parts of the toilet training pad. It should be recognized that the astringent agent may also be introduced into other layers of a toilet training pad such as a surge layer, a transfer layer, or a tissue layer, should the pad be comprised of numerous layers. Typically, if the astringent agent or source thereof is introduced onto or into a face of the liner, it is introduced onto or into the face of the liner which will ultimately face the wearer's skin. If the astringent agent or source thereof is introduced into or onto a face of the absorbent core, it is again generally introduced on the face which will ultimately face the wearer's skin. When astringents are introduced into or onto the absorbent core, a greater amount of liquid will generally be required to transport the astringent agents through the liner and next to the wearer's skin where the tingling or other sensation occurs. In a particular embodiment the astringent agent or source thereof of the present invention can be placed on the toilet training pad and the pad positioned such that the astringent agent is present in the crotch region of the wearer. Because the crotch region is the area of the body where the fluid is produced, the wearer will be alerted quickly upon urination as the astringent agent will contact the skin. Further, the crotch region contains a large number of nerve endings which can be stimulated by the astringent agent upon urination. In another embodiment, the astringent agent and toilet training pad can be located in the buttocks area. In another embodiment, the astringent agent and pad may be located in both the crotch area and the buttocks area for maximum tingling or other sensation.

Although the specific astringent agent utilized may affect the overall sensation felt by the wearer upon urination, the amount of sensation, or tingling, produced by the astringent agent is typically a direct result of the amount of astringent agent utilized. A sufficient amount of astringent agent should be utilized such that the wearer can feel a tightening of the skin sensation in the crotch, buttocks, or crotch and buttocks area of the body. Generally, a greater amount of astringent agent will be required to increase the sensation felt by the wearer when the intended wearer is a small child.

Typically, the astringent agents of the present invention are not simply introduced into or onto the toilet training pad of the present invention without a stabilizing mechanism to ensure the astringent agents stay in the desired area. The astringent agents or sources thereof of the present invention may be introduced into or onto a part or the entire liner, absorbent core, or another layer of the toilet training pad of the present invention utilizing various methods including, for example, spray coating, slot coating and printing, or a combination thereof. In spray coating, either liquid or solid astringents, neat or microencapsulated, are first thoroughly mixed with a substantially urine-soluble or urine-dispersable adhesive agent to disperse the astringent agents throughout the adhesive material. The adhesive material can comprise a urine-soluble adhesive which will partially or completely dissolve upon urination by the wearer and allow release of the astringent agent, or may be comprised of a material which disperses upon contact with urine allowing release of the astringent agent. Suitable urine-soluble adhesives include, for example, polyvinyl pyrrolidone and polyvinyl alcohol, and combinations thereof. After the adhesive and astringent agent are thoroughly mixed, they can be applied by, for example, spraying, knifing, or roller coating, onto the desired area of the toilet training pad of the present invention and allowed to dry. The adhesive-astringent agent mixture, 46 in FIG. 1B, adheres to the liner, absorbent core, or another layer where it is stable until urination occurs by the wearer. Upon urination, the adhesive releases the astringent agent such that it may contact the skin of the wearer. Typically, the astringent/adhesive mixture comprises from about 5% to about 50% astringent by weight, preferably from about 10% to about 40% astringent by weight. It will be recognized by one skilled in the art that the mixture ratio of the astringent and adhesive may vary depending upon the material construction upon which the mixture is applied. In a particular embodiment, a first layer comprising an astringent agent or a source thereof and an adhesive are sprayed onto the substrate. After the first layer has dried, a second layer comprising an adhesive agent is sprayed on top of the first layer. This combination of two layers, including a second layer comprised of an adhesive may help ensure that the astringent agent does not contact the skin of the wearer prior to urination.

Similar to spray coating, astringent agents may be introduced into or onto the toilet training pad of the present invention through slot coating. In slot coating, an adhesive-astringent mixture as discussed above is introduced directly onto the desired area of the pad in "slots," discrete row patterns, or other patterns. Upon urination by the wearer, the adhesive allows a release of the astringent such that it may contact the skin of the wearer. Slot coating may be advantageous in certain applications where it is not desirable to coat the entire surface with an adhesive. In some circumstances, an adhesive coating over an entire surface may retard quick absorption of the urine into the absorbent core. When slot coating is utilized, channels are created where no adhesive is present and urine may drain quickly.

Slot coating may also be advantageous in certain applications where precise control of the location of the astringent agent is desired. Typically, the rows of astringent/adhesive are spaced on the order of from about 0.1 inches to about 3 inches apart from each other, preferably from about 0.2 inches to about 2 inches apart from each other, and most preferably about 0.25 inches apart from each other. Generally, the rows are evenly spaced across the surface upon which they are applied, but may be spaced in specific patterns with varying spacing if desired. As described above in regard to spray coating, a second layer of adhesive may be introduced on top of a first slot-coated layer comprising both an astringent and an adhesive to further ensure that the astringent agent does not contact the skin of the wearer prior to urination.

The astringent agent or source thereof can also be introduced onto or into a gas permeable liner, absorbent core, or another layer of the training pad of the present invention through the use of a vacuum driving force or through the use of a pressure differential. When utilizing a vacuum force, the astringent agent or source thereof is positioned on the liner, absorbent core, or another layer while a vacuum driving force is applied to the opposite side of the liner or core to drive the astringent agent into the fabric matrix of the liner, core, or other layer. Varying degrees of vacuum can be applied depending upon the required depth of the astringent agent. In this embodiment, no urine-soluble adhesive is necessary. Once in the fabric matrix of the pad, the astringent agent or source thereof is stable until urination occurs and the astringent agent is transported to the wearer's skin. This embodiment is particularly useful for solid or powdered astringent agents which are applied neat. Alternatively, electrostatic forces or other means may be utilized to stabilize the astringent on the surface of the liner or core.

In an alternative embodiment of the present invention, the astringent agent or source thereof may be incorporated into a hydrophilic microsponge material which is subsequently used in combination with the pad of the present invention. The microsponge performs the same function as the microencapsulation shell material and keeps the astringent agent from contacting the wearer's skin until urination has occurred. The hydrophilic microsponge containing the astringent agent or source thereof is introduced onto or into the toilet training pad of the present invention as discussed above. Suitable materials comprising the hydrophilic microsponge include, for example, acrylate polymers and acrylate copolymers of a hydrophilic nature. To incorporate either a solid or a liquid astringent agent into the hydrophilic microsponge material, the astringent agent can be introduced into an suitable volatile, such as an alcohol or water and dissolved. The solution containing the dissolved astringent agent is contacted with and absorbed into the microsponge material. After absorption, the solvent is driven off by evaporation or other means known in the art, leaving a dry hydrophilic microsponge material containing the astringent agent. Because of the structure of the sponge, the astringent agent is suitably stable as it would need to travel a tortuous path to exit the sponge. The astringent is located in the interstitial spaces in the sponge and, upon flooding of the sponge upon urination, is driven out of the interstitial spaces by the urine and can contact the skin of the wearer. The astringent-containing hydrophilic microsponges of the present invention may be introduced onto or into the toilet training pad of the present invention similar to the encapsulated astringents discussed above.

Figure 2:
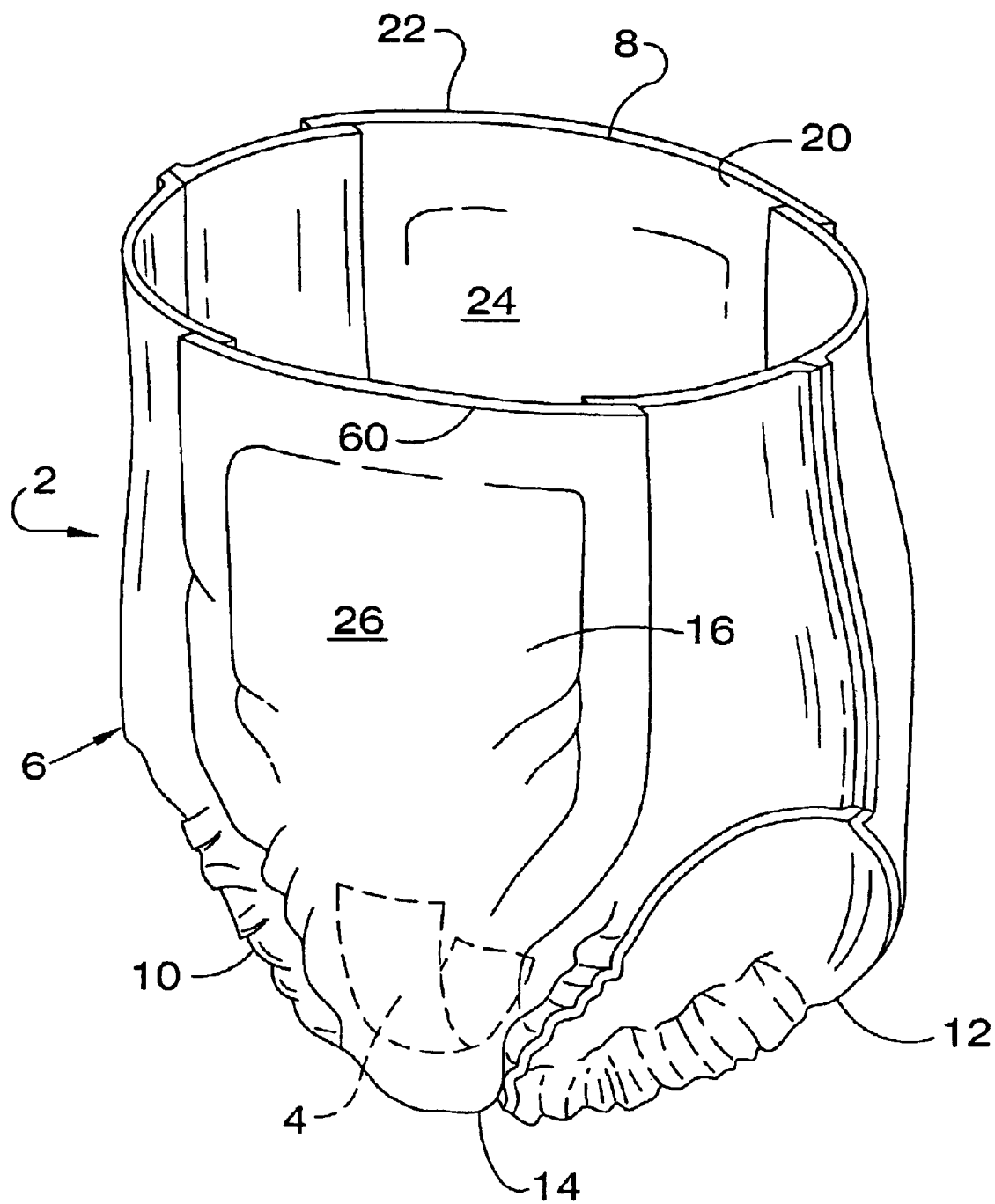
FIG. 2 is a perspective view of a disposable toilet training article in accordance with the present invention, which includes a pliable toilet training pad.

Referring now to FIG. 2, there is shown a toilet training article 2 for purposes of illustration of a toilet training pad 4 of the present invention which is attached to the inside of a three-dimensional, disposable, toilet training pant 6. The toilet training pad 4 contains an astringent agent or source thereof in accordance with the present invention to alert the wearer when urination has occurred by allowing the astringent agent to contact the skin and create a tingling or other sensation on the wearer's skin.

Although the toilet training pad in FIG. 2 is illustrated as part of toilet training pants, the training pad may also be used in conjunction with other garments, such as underwear, diapers, diaper pants, washable or reusable absorbent garments such as cloth training pants, plastic training pants, or the like. The astringent containing toilet training pad may either be part of the garment as a whole (i.e., integrated into the garment when manufactured) or may be in the form of an insert which may be permanently or releasably attached to any of the aforementioned garments by the manufacturer or the consumer. If the toilet training pad containing the astringent agent or source thereof is manufactured in the form of an insertable pad, it preferably has attachable means thereon to allow the consumer to easily attach the pad to an undergarment. Suitable attachable means may include, for example, adhesive strips, thermal bonds, ultrasonic bonds, hook and loop type fasteners, other attachments, etc. This allows the consumer the choice of the type of garment to use with the toilet training pad of the present invention. Also, the consumer can control when the toilet training pad is used.

Referring again to FIG. 2, the training pant 6 is a three-dimensional garment and defines a waist opening 8 and two leg openings 10 and 12. A crotch region 14 is generally located between the leg openings 10 and 12 and comprises that portion of the training pant which, when worn, is positioned between the legs of the wearer and covers the lower torso of the wearer. The crotch region is typically where the toilet training pad containing the astringent agent or source thereof is located. A front waist region 16 of the training pants generally extends from the crotch region 14 to a front end 60 of the pants, and a back waist region 20 extends from the crotch region 14 to a back end 22 of the pants. The training pant 6 also includes an inner surface 24 and an opposite outer surface 26. By way of illustration only, various materials and methods for constructing training pants are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference. When the training pant is worn, the toilet training pad is positioned near or against the skin of the wearer and located so that urine contacts the toilet training pad during urination. The toilet training pad or toilet training pad area, which may encompass both the crotch region and the buttocks region, contains the astringent agent in accordance with the present invention.

In view of the above, it will be seen that the several embodiments of the invention are achieved. As various changes could be made in the above-described toilet training pad without departing from the scope of the invention, it is intended that all matter contained in the above description be interpreted as illustrative and not in a limiting sense.

What is claimed is:

1. A process for manufacturing an article, the article in the form of a pad comprising a pliable substrate and an astringent agent or source thereof, the process comprising:

mixing the astringent agent or a source thereof with a urine-soluble or urine-diapersable adhesive; and applying the resulting mixture to the substrate and allowing the mixture to dry.

2. The process as set forth in claim 1 wherein the resulting mixture is sprayed on the substrate.

3. The process as set forth in claim 1 wherein the resulting mixture is applied to the substrate by knifing.

4. The process as set forth in claim 1 wherein the resulting mixture is applied to the substrate by roller coating.

5. The process as set forth in claim 1 wherein the adhesive is selected from the group consisting of polyvinyl pyrrolidone, and polyvinyl alcohol.

6. The process as set forth in claim 1 wherein the substrate is of layered construction and comprises a liner and an absorbent core layer.

7. The process as set forth in claim 6 wherein the mixture of the astringent agent or source thereof and adhesive is sprayed onto the liner.

8. The process as set forth in claim 6 wherein the mixture of the astringent agent or source thereof and adhesive is sprayed onto the absorbent core layer.

9. The process as set forth in claim 1 wherein the astringent agent is encapsulated in a shell material that when wetted with urine allows a release of the astringent material.

10. The process as set forth in claim 9 wherein the shell material comprises a material selected from the group consisting of ethyl cellulose, starches, sugars, dextrins and cyclodextrins.

11. The process as set forth in claim 1 wherein the astringent agent is incorporated in a hydrophilic microsponge material.

12. The process as set forth in claim 1 wherein mixture is comprised of from about 5% to about 50% by weight of astringent agent.

13. The process as set forth in claim 1 wherein the mixture is comprised of from about 10% to about 40% by weight of astringent agent.

14. The process as set forth in claim 1 wherein the mixture is sprayed onto the substrate in rows spaced from about 0.1 inches to about 3 inches apart.

15. The process as set forth in claim 1 wherein the mixture is sprayed onto the substrate in rows spaced about 0.25 inches apart.

16. The process as set forth in claim 1 wherein the mixture is a first mixture and a second mixture comprising an adhesive is sprayed on top of the first mixture.

17. The process as set forth in claim 1 wherein the astringent agent or source thereof is selected from the group consisting of *acacia concinna* extract, aluminum citrate, aluminum lactate, apple (*pyrus malus*) extract, *astragalus sinicus* extract, *astrocaryum murumuru* extract, *astrocaryum tucuma* extract, *azadirachta indica* extract, azelamide MEA, bearberry (*arctostaphylos uva-ursi*) extract, birch (*betula alba*) leaf extract, *catalpa kaempfera* extract, *celastrus paniculata* extract, chinese hibiscus (*hibiscus rosa-sinensis*) extract, *coccinea indica* extract, coffee (*coffea arabica*) bean extract, elder (*sambucus nigra*) oil, *euterpe precatoria* extract, evening primrose (*oenothera biennis*) extract, eyebright (*euphrasia officinalis*) extract, gentian (*gentiana lutea*) extract, *geranium maculatum* extract, grape (*vitis vinifera*) leaf extract, henna (*lawsonia inermis*) extract, *hierochloe odorata* extract, honeysuckle (*lonicera caprifolium*) extract, hops (*humulus lupulus*) extract, horsetail (*equisetum arvense*) extract, ivy (*hedera helix*) extract, jujube (*zizyphus jujuba*) extract, *juniperus communis* extract, *kadsura heteliloca* extract, kola (*cola acuminata*) extract, lady's mantle (*alchemilla vulgaris*) extract, lemon bioflavonoids extract, lemon (*citrus medica limonum*) extract, lemon (*citrus medica limonum*) peel extract, *lysimachia foenum-graecum* extract, magnolia spp. extract, *mauritia flexosa* extract, *maximilliana regia* extract, *melaleuca uncinata* extract, *melaleuca wilsonii* extract, *melia australasica* extract, mentha spp, neem (*melia azadirachta*) seed oil, nettle (*urtica dioica*) extract, oak (quercus) bark extract, palmetto extract, passionflower (passiflora) fruit extract, *phyllanthus emblica* extract (or *emblica officinalis*), plantain (*plantago major*) extract, *polygonum multiflorum* extract, *pterocarpus marsupianus* extract, raspberry (rubus) extract, selinum spp. extract, *shorea robusta* extract, St. John's wort (*hypericum perforatum*) extract, tannic acid, tea (*camellia sinensis*) extract, *vetiveria zizanoides* extract, walnut (*juglans regia*) leaf extract, walnut (*juglans regia*) oil, wheat (*triticum vulgare*) protein, white nettle (*lamium album*) extract, witch hazel (*hamamelis virginiana*) extract, *xanthozylum bungeanum* extract, zinc lactate, zinc oxide, calcium chloride, aluminum lactate, ammonium alum, potassium alum, sodium alum and combinations thereof.

18. The process as set forth in claim 1 wherein the astringent agent or source thereof is selected from the group consisting of calcium chloride, aluminum lactate, ammonium alum, potassium alum, sodium alum and combinations thereof.

* * * * *